United States Patent [19]

Allmér

[11] Patent Number: 5,051,312

[45] Date of Patent: Sep. 24, 1991

[54] MODIFICATION OF POLYMER SURFACES

[75] Inventor: Klas G. M. Allmér, Stockholm, Sweden

[73] Assignee: E. I. Du Pont de Nemours and Company, Wilmington, Del.

[21] Appl. No.: 500,830

[22] Filed: Mar. 29, 1990

[51] Int. Cl.$^5$ .............................................. B32B 15/08
[52] U.S. Cl. ....................... 428/458; 264/22; 427/2; 427/53.1; 427/54.1; 428/463; 522/14; 522/120; 522/126; 522/127; 522/129; 522/134
[58] Field of Search .................. 427/53.1, 54.1, 437, 427/2; 522/14, 120, 126, 127, 129, 134; 264/22, 25; 428/458, 457, 463

[56] References Cited

U.S. PATENT DOCUMENTS

| | | | |
|---|---|---|---|
| 2,789,063 | 4/1957 | Purvis et al. | 117/47 |
| 3,563,871 | 2/1971 | Newman et al. | 204/159.14 |
| 4,164,463 | 8/1979 | Fang | 204/296 |
| 4,309,453 | 1/1982 | Reiner et al. | 522/126 |
| 4,824,692 | 4/1989 | Gillick et al. | 427/53.1 |
| 4,839,261 | 6/1989 | Nakazaki et al. | 522/120 X |

OTHER PUBLICATIONS

S. Tazuke et al., American Chemical Society Symposium Series, vol. 121 (1980), pp. 217–241.

Primary Examiner—Michael Lusignan

[57] ABSTRACT

This invention concerns a process for modifying polymer surfaces by contacting the surface with a selected organic modifying agent while irradiating the surface with ultraviolet and/or visible light that can be absorbed by the modifier. Patterns of modified and unmodified surfaces can be produced. Polymers with modified surfaces are useful for absorbing biologically active molecules, composites, printing plates and electronics.

37 Claims, No Drawings

MODIFICATION OF POLYMER SURFACES

FIELD OF INVENTION

The invention concerns a process for modifying polymer surfaces, modified by exposure to ultraviolet and/or visible radiation while such surfaces are in contact with modifiers, which are selected organic compounds. Polymers with modified surfaces may be used to absorb biologically active molecules, may exhibit improved adhesion, useful in composites, and since the process may be used to produce patterns or images on the polymer surface, are useful in printing processes and electronics.

BACKGROUND OF THE INVENTION

Modification of polymer surfaces by various methods has been practiced for many years. For example, U.S. Pat. No. 2,789,063 describes the use of a sodium/naphthalene reagent to treat poly(tetrafluoroethylene) (PTFE), to modify the surface properties. Numerous other methods have been described using other reagents to chemically modify the surface of various polymers. In addition, other methods of physical treatment, sometimes in the presence of various reagents, have also been used, such as laser ablation, exposure to various plasmas, exposure to electron beams, etc. Some of these methods are capable of forming an image (modified vs. unmodified) on the polymer surface.

U.S. Pat. No. 4,164,463 describes the modification of perfluorocarbon (optionally containing bromine and chlorine atoms) polymer surfaces using sulfur or phosphorous containing compounds. There are several methods of modifying the surfaces disclosed in this patent, among them (at column 8, lines 14–16) the use of "ultraviolet light" to promote the process. It is stated that the "fluoropolymer is exposed to radiation" (as opposed to the instant process where the modifier absorbs the actinic radiation, infra), and it also states that "The amount of solution or liquid in which the fluoropolymer is placed should be such that the starting material is thoroughly wetted, but not so much that the passage of radiation through the liquid is impeded." In the present process it is the modifier which is "activated" by absorbing the actinic radiation (infra).

U.S. Pat. No. 3,563,871 describes the modification of a polychloroprene rubber surface by exposure to radiation with a wavelength of 200 to 350 nm in the absence of oxygen. No other organic compound is present as a modifier.

U.S. Pat. No. 4,824,692 describes the modification of the surface of an ethylenically unsaturated rubber by irradiation of wavelength 100 to 700 nm radiation the presence of selected alkyl halides.

S. Tazuke, et. al., American Chemical Society Symposium Series, vol. 121, Washington, DC, 1980, pp. 217–241, describe the use of photografting to modify polymer surfaces. In this technique a polymerizable vinyl monomer is contacted with a polymer surface and optionally a sensitizer, and the vinyl monomer is grafted to and polymerized on the surface of the polymer, thereby modifying the surface. In the present process, readily polymerizable vinyl monomers are not used as modifying compounds.

It is the object of this invention to provide a process for the modification of various polymer surfaces which is capable of producing images on the polymer surfaces, and which uses ultraviolet and/or visible radiation, which is easy and inexpensive to generate.

SUMMARY OF THE INVENTION

A process is provided wherein polymer surfaces are modified by exposure to ultraviolet/visible radiation in the presence of selected organic modifiers. The polymers surfaces are reduced by the modifiers, and in some cases the modifiers may be grafted onto the surfaces. Such surfaces have properties, such as hydrophilicity and adhesion, altered from those of the bulk polymer. Patterns of modified and unmodified polymer surfaces may be produced. Polymers with modified surfaces are useful as printing plates, in electronics and in composites.

DETAILS OF THE INVENTION

This invention concerns a process for modifying polymer surfaces, comprising, exposing an organic modifier to actinic radiation while a polymer surface is in contact with said organic modifier, provided that the oxidation potential of the modifier minus the reduction potential of the polymer minus the excitation energy of the modifier is less than zero, further provided that said actinic radiation is of a wavelength that is absorbed by said modifier, and further provided said polymer does not contain ethylenic unsaturation.

Any polymer may be used in the above process, provided the limitation concerning the polymer reduction potential (infra) is met, and provided the polymer does not contain ethylenic unsaturation, that is alkenyl double bonds. Preferred polymers are fluorinated polymers, polyimides and polyesters. Especially preferred polymers are perfluorinated polymers (those containing less than 0.5% by weight hydrogen and may contain chlorine or bromine in place of fluorine). Most preferred polymers are perfluorinated polymers and copolymers of tetrafluoroethylene. Polymers whose glass transition temperature and/or crystalline melting point are above ambient temperature (plastics) and elastomers are useful in this process. The elastomers may be cured or uncured.

Reduction potentials (usually expressed in volts) of polymers can be determined in several ways, especially electrochemically. See for example reduction potential of PTFE, D. J. Barker, Electrochmica Acta, vol. 23, pp. 1107–1110 (1978) and D. M. Brewis, Die Angwandte Makromolekulare Chemie, vol. 43, pp. 191–194 (1975), and the reduction potential of the polyimide from oxydianiline and pyromellitic anhydride, S. Mazur and S Reich, J. Phys. Chem., vol. 90, pp. 1365–1372 (1986). If the reduction potential of any particular polymer has not been measured, an approximation can be made by using the reduction potential of a model compound which is structurally similar to the polymer. The reduction potential of a large number of organic compounds has been compiled by Meites, et al., infra. As is well known to those skilled in the art, these reduction potentials may vary somewhat with various experimental parameters, such as the solvent used.

By actinic radiation is meant electromagnetic radiation in the ultraviolet and visible portions of the spectrum, that of wavelengths from about 200 nm to about 700 nm. The particular wavelength of actinic radiation chosen must correspond to one or more wavelengths that are absorbed by the modifier. Absorption spectra of many organic compounds are commonly available, or may be measured by methods well known to those skilled in the art. In practice, sources of actinic radiation often have multiple or continuous wavelength outputs. Such sources are suitable so long as at least some of their output is at wavelengths that are absorbed by the modifier. There are many ways of generating such radiation, for example a medium pressure mercury lamp is commonly used.

The modifier is an organic compound that absorbs actinic radiation and whose oxidation potential minus the reduction potential of the polymer minus the excitation energy of the modifier is less than zero. Thus, there are two criteria for the modifier that must be considered in this limitation, namely the oxidation potential and excitation energy of modifier. Oxidation potentials of organic compounds can be determined by methods known to those skilled in the art, for example by polarography. The oxidation potential of many organic compounds have been determined, and a large compilation has been made by L. Meites, P. Zuman and (in part) E. Rupp, CRC Handbook Series in Organic Electrochemistry, Vol. 1–6, CRC Press, Inc. Cleveland, Ohio and Boca Raton, Florida, published 1977–1983, which are hereby included by reference.

The "excitation energy" of the modifier is the energy of the lowest lying triplet state of the modifier molecule, expressed in electron volts. The measurement of such energies is known to those skilled in the art, for example R. S. Becker, Theory and Interpretation of Fluorescence and Phosphorescence, Wiley Interscience, New York, 1969, chapter 7, and D. 0. Cowan and R. L. Drisko, Elements of Organic Photochemistry, Plenum Press, New York, 1976, chapter 5.2. An extensive listing of triplet state energies is found in S. L. Murov, Handbook of Photochemistry, Marcel Dekker, Inc., New York, 1973, pp. 3–25, which is hereby included by reference. In addition, the reduction potential of the modifier in the ground state should be lower than the reduction potential of the polymer, otherwise the modifier will react with itself, and not the polymer. Reduction potentials of organic compounds are found in Meites, et. al., supra.

The modifier in the present reaction does not have any substantial reaction with the polymer (surface) in the absence of actinic radiation. Thus the use of chemical modifiers that act without actinic radiation, such as sodium/naphthalene with PTFE, are not contemplated by this invention. Some modifiers may act with or without actinic radiation. They may, for example, for relatively short time periods and low (ambient) temperatures not modify polymer surfaces except upon exposure to actinic radiation, but under other conditions, such as longer time periods and/or higher temperatures, modify polymer surfaces without actinic radiation. When used under conditions under which such modifiers are not effective without actinic radiation, such modifiers are included within the instant process, but when used under conditions under which polymer surfaces are modified without actinic radiation, are not included in the instant process.

The modifiers as used herein are not vinyl monomers readily polymerized by free radicals. It is known in the art that polymer surfaces may be grafted (see Tazuke, et. al., supra) with polymerizable vinyl monomers by exposing such polymer surfaces to the monomers in the presence of a suitable radical generating agents such as a peroxide, ionizing radiation or actinic radiation. Typical vinyl monomers that are not included within the scope of the modifiers herein include acrylic acids, esters and amides, styrene, acrylonitrile, vinyl chloride, etc. Other free radically polymerizable vinyl monomers are known to those skilled in the art.

Preferred modifier/polymer combinations useful in the present invention include: perfluorinated polymers and copolymers of tetrafluoroethylene with the 4-hydroxybenzenethiol dianion, p-aminobenzenethiol anion, benzenethiol anion, the dianion of HSCHRCHROH where R is hydrogen or methyl, the anion of 2,5-pentanedione, the anion of diphenylcarbinol, 2-mercaptoethanol, tetrachlorohydroquinone, 4-aminofluorene, phenylthiazine, cis-stilbene, vanillin, the anion of 2-mercaptoethanol, the anion of 2-naphthol, the anion of dibenzoylmethane, the dianion of ethylene glycol, and N,N,N'N'-tetramethyl-p-phenylenediamine; polyimide based on oxydianiline and pyromellitic anhydride with 4-aminofluorene, the dianion of ethylene glycol, the dianion of 3-hydroxybutane-3-thiol, and vanillin (4-hydroxy-3-methoxybenzaldehyde); poly(ethylene terephthalate) with the anion of 4-aminobenzenethiol; and a copolymer of TFE with perfluoro(2,2-dimethyl-1,3-dioxole) with N,N,N',N'-tetramethyl-p-phenylenediamine. An especially preferred modifier/polymer combination is a copolymer of TFE with perfluoro(2,2-dimethyl,3-dioxole) and N,N,N',N'-tetramethyl-p-phenylenediamine. In the above combinations, if a modifier is an anion, an appropriate metal cation is a counterion. Alkali metal cations are preferred.

The modifier and polymer may be brought into contact by a variety of means. For example, the modifier may be dissolved in an inert solvent, the solution being contacted with the polymer surface. Alternatively, a thin layer of the modifier may be coated onto the polymer surface or the polymer surface may be exposed to modifier vapor. It is preferred if the polymer surface is contacted with a modifier in solution. The solvents for such solutions should not absorb actinic radiation at the same wavelength as the modifier, so that any actinic radiation applied may reach and activate the modifier. Also the reduction potential of the solvent should be below that of the polymer, so that the polymer and not the solvent reacts with the modifier. Preferred solvents are polar aprotic solvents that meet the above conditions. Especially preferred solvents (where appropriate) are N,N-dimethylformamide, dimethylsulfoxide, acetonitrile and dimethylacetamide. Water and alcohols are also preferred solvents. The solvent should not dissolve the polymer. Typical concentrations of modifier in solvent are about 0.001 to about 0.2M. Preferred concentrations of modifier are about 0.025 to about 0.1M. The solution layer (or coated layer or vapor space) between the light source and the polymer surface should be relatively thin, so that as much of the absorbable (by the modifier) actinic radiation as possible reaches the modifier very close to the polymer surface. It is believed that the "activated" modifier molecules, that is those that have absorbed actinic radiation, have a short lifetime, and only those modifier molecules that absorb actinic radiation close to the polymer surface actually are effective in modifying the polymer surface.

The process may be run in any apparatus suitable for containing the polymer piece(s) and the modifier. If the polymer pieces are simply coated with the modifier, the coated polymer may be directly exposed to the actinic radiation. If modifier solution or vapor must be contained, the container must be transparent to actinic radiation of the wavelength absorbed by the modifier, or the actinic radiation source must be inside the container. A container material transparent to actinic radiation of the wavelength range of the process is fused quartz.

Temperature and pressure are not critical, and the process is conveniently run at ambient conditions.

While modifier/polymer combinations meeting the criteria of the process have been found to be operative, it has also been found that some modifier/polymer combinations are more efficient than others. By efficiency in this context is meant the ability to modify the polymer surface under given conditions in a specific amount of time. A semiquantitative measure of surface modification can be obtained by measurement of a surface property, such as the contact angle of the surface with a given liquid. The relative efficiency of any particular modifier/polymer pair under a given set of conditions cannot be predicted, but can be determined by simple experimentation (see for instance, Examples 1–14). It is believed that in efficient systems the modifier oxidation potential minus the reduction potential of the polymer minus the excitation energy of the modifier is more negative than about −0.5 volt, and such modifier/polymer combinations are preferred. It is also believed that, when the modifier contacts the polymer as a solution or liquid, the surface modification process is more efficient if the solution wets the polymer surface well.

Optionally, compounds herein termed accelerators may be used in the process. While these accelerators are not in themselves modifiers (they do not modify the polymer surface in the presence of actinic radiation), their presence in the process accelerates or makes the process more efficient. It has been found that certain aromatic compounds such as benzophenone, thioxanthon, and naphthalene are effective and preferred accelerators. Typical concentrations for accelerators are about 0.001 to about 0.1M. It has been found that when accelerators are used, actinic radiation that can be absorbed by the accelerator and/or modifier is effective in modifying the polymer surface. Accelerators are not polymerizable vinyl monomers (supra).

By masking or blocking out the actinic radiation from a portion of the polymer surface (or more correctly, modifier near the polymer surface), it is possible to create patterns on the polymer surface consisting of modified and unmodified surface. Of course the unmodified surface will exist where the modifier near the surface was not exposed to the actinic radiation. Using a relatively crude apparatus, resolution as small as 0.1 mm was obtained, see Example 46. Varying degrees of surface modification may be obtained by partially filtering the actinic radiation, so that different intensities of actinic radiation are obtained over different parts of the polymer surface. The same effect can be obtained by varying the exposure time to actinic radiation.

It has, surprisingly, been found that the modified polymer surfaces in many cases are either colorless or only lightly colored. This is in contrast to many processes which use powerful chemical reductants, such as sodium/naphthalene with PTFE, where intense dark surface colors are generated. This is an advantage for the instant process, when surface color is important.

Polymers with modified surfaces are useful as printing plates, in electronics, composites (where improved adhesion to the polymer surface is required), for immobilizing biologically active molecules (see Example 21), for forming conductive surfaces, for forming antistatic surfaces, and for metalization (see Example 47).

EXAMPLES

In the following Examples, Teflon ® AF containing 70% fluorinated dioxazolane units was obtained from Du Pont. Polytetrafluoroethylene (PTFE), poly(tetrafluoroethylene co hexafluoropropylene) (Teflon ® FEP), and polyimide based on pyrometallic dianhydride and oxydianiline (Kapton ®) are available commercially from E. I. du Pont de Nemours & Company, Wilmington, Del. and were used as received.

The organic sodium salts were prepared by reacting the compounds with sodium methoxide in methanol solution with subsequent evaporation and drying. All other reagents or solvents are available commercially and were used as received, except benzophenone which was recrystallized from methanol.

The following abbbreviations for the modifiers are used:

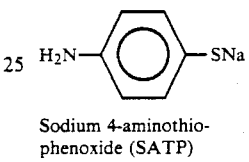

Sodium 4-aminothiophenoxide (SATP)

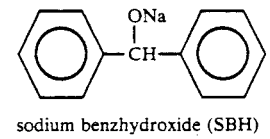

sodium benzhydroxide (SBH)

$$\begin{array}{c} \text{SNa} \\ | \\ \text{CH}_3\text{CHCHCH}_3 \\ | \\ \text{ONa} \end{array}$$

disodium 2-mercapto-3-butoxide (DSMB)

NaSCH$_2$CH$_2$ONa disodium 1-mercapto-2-ethoxide (DSME)

$$\begin{array}{c} \text{ONa} \quad \text{O} \\ | \qquad \| \\ \text{CH}_3\text{C}=\text{CHCCH}_3 \end{array}$$

sodium salt of 2,4-pentanedione (SPD)

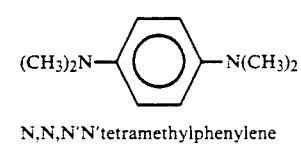

N,N,N'N'tetramethylphenylene diamine (TMPDA)

EXAMPLES 1–14

In a quartz beaker with a flat bottom, a PTFE film (2×3 cm) was placed onto a frame made of alumina foil. The PTFE film was pressed down against the bottom by applying a flat piece of glass over it as weight. The solution containing donor and optionally accelerator was prepared and nitrogen was bubbled through for 10 minutes. This solution was then added to the quartz beaker, the beaker was flushed with nitrogen, and then it was placed above a 100 W medium pressure mercury lamp with main emittance at 366 nm. After UV exposure, the film was taken out of the beaker, rinsed in acetone, immersed in boiling water for 1 hour, and then Soxhlet extracted with tetrahydrofuran for 18 hours.

The parts of the film which were exposed to UV light had improved wetting and usually got colored, ranging from weak yellow to black, while parts which were shielded from UV light remained hydrophobic and colorless. When the samples were treated with boiling water, the colored areas got fainter and turned brown/yellow.

Advancing contact angle was measured by applying a 10 μl water droplet on the PTFE surface and measuring the diameter of the surface [Dahlgren, Journal of Immunological Methods, 40, 171-179 (1981)]. Results are given in Table 1.

gen, and placed above a 100 W medium pressure mercury lamp for 3 hours. After exposure the Teflon ® AF

TABLE 1

| Example | Modifier | Solvent | Accelerator | Exposure (min) | Contact Angle against water | Surface Composition from ESCA (%) | | | | |
|---|---|---|---|---|---|---|---|---|---|---|
| | | | | | | F | C | O | N | S |
| 1 | SBH (S) | DMF | — | 60 | 73° | 34 | 53 | 10 | 1.5 | — |
| 2 | SBH(S) | isopropanol | — | 60 | 74° | | | | | |
| 3 | DSMB(S) | DMF | — | 60 | 49° | 5.3 | 67 | 19 | 1 | 6 |
| 4 | DSMB(S) | DMF | — | 2 | 79° | | | | | |
| 5 | DSMB(S) | DMF | benzophenone (0.025M) | 2 | 71° | | | | | |
| 6 | SATP (0.025M) | DMF | — | 10 | 71° | 10 | 67 | 15 | 3.7 | 3.9 |
| 7 | SATP (0.025M) | DMF | — | 60 | 51° | 10 | 68 | 14 | 3.9 | 4.8 |
| 8 | SATP(S) | acetonitrile | — | 60 | — | 6.7 | 63 | 13 | 3.7 | 3.4 |
| 9 | SPD (0.05M) | DMF | — | 60 | 72° | 30 | 48 | 13 | 0.4 | 0.2 |
| 10 | SPD (00.05M) | isopropanol | — | 60 | — | 39 | 44 | 10 | 0.3 | 0.1 |
| 11 | DSME(S) | DMF | — | 60 | 72° | 26 | 54 | 14 | 1.1 | 3.6 |
| 12 | DSME(S) | DMF | naphtalene (0.05M) | 60 | 62 | 5.7 | 62 | 26 | 0.7 | 4.9 |
| 13 | DSME(S) | DMF | triphenylene (0.05M) | 60 | 55° | | | | | |
| 14 | Untreated | PTFE | — | — | 115° | 68 | 31 | 0.2 | 0.1 | — |

EXAMPLE 15

A piece of PTFE film (10×15 cm) was put in a transparent low density polyethylene (LDPE) bag (15×20 cm) with a zip-lock. A solution containing 15 ml DMF, 0.045 g DSMB and 0.068 g benzophenone was added to the bag. The bag was flushed with nitrogen for 1 minute, sealed and placed horizontally. An aluminum frame and quartz glass was placed above the bag. The bag was exposed to UV light for 10 minutes from a 100 W medium pressure lamp situated 10 cm from the bag. After exposure, the PTFE film was rinsed with acetone, immersed in hot water for 60 minutes and Soxhlet extracted with THF for 18 hours. The film was gray colored on the areas exposed to UV light, the gray area got brown/yellow after water treatment. The contact angle against water of the exposed film was 56°, a decrease of about 60° compared to untreated PTFE.

EXAMPLE 16

A piece of Teflon ® FEP (a copolymer of TFE and hexafluoropropylene) film (10×15 cm) was put in a transparent LDPE bag (15×20 cm) with a zip-lock. A solution containing 15 ml DMF 0.09 g DSMB and 0.068 g benzophenone was added to the bag. The bag was flushed with nitrogen for 1 minute, sealed and placed horizontally. An aluminum frame and quartz glass was placed on top of the bag. The bag was exposed to UV light for 30 minutes from a 100 W medium pressure lamp situated 10 cm from the bag. After exposure, the PTFE film was rinsed with acetone and immersed in hot water for 60 minutes. The film was faint 9ray/-brown color in the areas exposed to UV light, turning weakly yellow after water treatment. The contact angle of a 25/75 ethanol/water mixture decreased from 70° to 42° by this treatment.

EXAMPLE 17

A piece of Teflon ® AF [copolymer of TFE and perfluoro(2,2-dimethyl-1,3-dioxole)]film was put in a quartz beaker on top of an aluminum frame with a flat piece of glass above as weight. A solution containing 50 ml DMF, 0.37 g SATP and 0.82 g TMPDA was added to the quartz beaker. The beaker was flushed with nitrogen, and placed above a 100 W medium pressure mercury lamp for 3 hours. After exposure the Teflon ® AF film was rinsed with acetone and immersed in hot water for 2 hours. The film was patchwise yellow on the exposed areas. The contact angle against a 25/75 ethanol/water mixture varied between 20°-40° on the areas exposed to UV light, untreated Teflon ® AF has a contact angle of 74°.

EXAMPLE 18

A piece of Kapton ® film (polyimide from oxydianiline and pyromettallic anhydride) (3×2 cm) was put in a quartz beaker on top of an aluminum frame with a flat piece of glass above as weight. A solution containing 50 ml DMF, 0.45 g 2-aminofluorene was added to the quartz beaker. The beaker was flushed with nitrogen, and placed above a 100 W medium pressure mercury lamp for 1 hour. After exposure the Kapton ® film was rinsed with acetone and water. The film got darker on the exposed areas, and the contact angle against water of the reduced film was 41°. A Kapton ® film which was immersed in the same reducing solution, but in dark for 72 hours had a contact angle of 64°.

EXAMPLE 18

A piece of Kapton ® film (3×2 cm) was put in a quartz beaker on top of a frame made from a transparent polyethylene film, and with a flat piece of glass above as weight. A solution containing 50 ml water, 0.45 g vanillin and 0.2 g sodium hydroxide was added to the quartz beaker. The beaker was flushed with nitrogen, and placed above a 100 W medium pressure mercury lamp for 30 minutes. After exposure the Kapton ® film was immersed in 0.01 M HCl(aq) for 1 hour, and then rinsed with water. The exposed film had a contact angle against water of 24°, while a film which had been treated the same way, but without UV exposure had a contact angle of 46°.

EXAMPLE 19

The PTFE film reduced in Example 3, was electroless plated with the following procedure:

The film was dipped in a water solution containing 0.1% PdC12 for 1 minute, dried, and then immersed in a 0.1 M NaBH4 solution for another minute. This activates the surface by depositing zero valent palladium onto the surface. The film was electroless plated with nickel by immersing in a 0.1 l water solution containing 2.38 g NiCl2, 2.12 g NaH2PO2xH2O, 25.4 g 50% gluconic acid, 5 ml NH4OH, and 2 g NaOH.

The film is only nickel plated on the areas which were exposed to UV light, the shaded surface areas remain hydrophobic PTFE even after the plating procedure.

The plated nickel adheres well enough to withstand a Scotch tape (Trademark, 3M Corp.) peel test.

EXAMPLE 20

A piece of PTFE film (10×15 cm) was put in a transparent LDPE bag (15×20 cm) with a zip-lock. To the bag 0.048 g DSMB in 15 ml DMF was added. The bag was flushed with nitrogen for 1 minute, sealed and placed horizontally. An aluminum frame and quartz glass was placed on top of the bag. The bag was exposed to UV light from a 100 W medium pressure lamp situated at cm distance. After exposure, the PTFE film was rinsed with acetone, then refluxed with NH3(aq) for 1 hour, and immersed in hot water for another hour.

The film was cut into 3×5 mm pieces, put in a vial and washed three times with N-dimethylformamide (DMF). After washing, the film pieces were put in 10 ml DMF solution containing 70 mg biotin-N-succinimide ester for 4 hours. The biotin treated film was washed with the following procedure:

3×20 ml DMF
3×20 ml water buffered to pH 7
3×20 ml water Containing 0.2 % Zonyl® FSN, available from E. I. du Pont de Nemours & Co., that has been purified 4×20 ml water buffered to pH 7

The PTFE film pieces was dried on paper, and transferred to a vial with 1.2 ml DMF containing 1.74 mg streptavidin and 60 ul 4-hydroxyazobenzene-2'-carboxylic acid. After 45 minutes, the absorbance at 500 nm was measured, and the amount of streptavidin bonded to the surface was calculated from a standard curve. To 1 g exposed PTFE 390 ng streptavidin was bonded, while to nonexposed PTFE only 260 ng was attached.

EXAMPLES 21-44

The procedure was the same as for Examples 1-14, but with polymers other than PTFE in some examples. Contact angle was usually measured with a water solution containing 25% ethanol, and the decrease in contact angle compared to a untreated polymer is given in the table. Modifier concentration is 0.05 M, or saturated solution (S). The results are shown in Table 2.

TABLE 2

| Example | Polymer | Modifier + Accelerator | Solvent | Exposure (min) | Decrease in Contact Angle |
|---|---|---|---|---|---|
| 21 | PTFE | Mercaptoethanol + 0.06% Naphtalene | THF | 60 | 7° |
| 22 | PTFE | Tetrachlorohydroquionone | DMF | 120 | 13° |
| 23 | PTFE | 2-Aminofluorene | DMF | 120 | 21° |
| 24 | PTFE | Phenylthiazine | DMF | 120 | 15° |
| 25 | PTFE | Cis-stilbene | DMF | 120 | 13° |
| 26 | PTFE | 2-Picoline | Water | 120 | 16° |
| 27 | PTFE | vanillin(S) | Water | 120 | 16° |
| 28 | PTFE | Sodiumthiophenoxide | DMF | 60 | 43° |
| 29 | PTFE | Monosodiummercaptoethanol | DMF | 60 | 40° |
| 30 | PTFE | N,N-dimethylaniline (0.1M) | DMF | 60 | 23° |
| 31 | Teflon ®-FEP | Sodiumthiophenoxide + benzophenone | DMF | 60 | 49° |
| 32 | Kapton ® | DSME(S) + Naphtalene | DMF | 60 | 26° |
| 33 | PTFE | Sodium 2-naphtenoxide (S) | DMF | 60 | 32° |
| 34 | PTFE | Disodium 4-hydroxythiphenoxide (S) | DMF | 60 | 67° |
| 35 | PTFE | Sodium salt of dibenzoylmethane (S) | DMF | 60 | 36° |
| 36 | PTFE | Sodium 4-amino thiophenoxide (S) | DMF | 60 | 55° |
| 37 | PTFE | N,N,N',N'-tetramethylphenylenediamine | DMF | 60 | 45° |
| 38 | PTFE | Disodiumethanthioxide (S) | DMF | 60 | 51° |
| 39 | Teflon ® AF | Disodiumethanthioxide (S) | DMF | 60 | 13° |
| 40 | Teflon ® AF | SATP (S) | DMF | 60 | 18° |
| 41 | Teflon ® AF | Disodium 4-hydroxythiophenoxide (S) | DMF | 60 | 15° |
| 42 | Kapton ® | Disodiumethanthioxide (S) + benzophenone | DMF | 30 | 18° |
| 43 | Kapton ® | TMPDA | DMF | 30 | 9° |
| 44 | Mylar ® | SATP | DMF | 60 | 11° |

EXAMPLE 45

A PTFE film was immersed for 15 minutes in a tetrahydrofuran (THF) solution containing 0.1 M TMPDA, then dried, first in air, then under vacuum for 15 minutes. The film was placed in a LDPE bag with zip-lock, flushed with nitrogen for 1 minute, and then sealed. The film in the LDPE bag was then exposed to UV light (366 nm) for 2 hours. This treatment gave a 22° decrease in contact angle, measured with 25% ethanol in water.

EXAMPLE 46

A PTFE film was placed in a LDPE bag (10×15 cm) with zip-lock and 15 ml of a DMF solution containing 0.1 M monosodiumthioethanol and 0.05 M thioxanthone was added. The bag was flushed with nitrogen for 1 minute, sealed, and the placed horizontally on a flat support. A patterned mask was placed above the LDPE film, and a quartz plate was placed over the mask. The PTFE film was exposed to UV light through the mask, and the areas exposed to UV light turned to a grey/yellow metallic looking surface with high wettability, while the areas shaded to UV light was colorless and hydrophobic. Even with this crude setup, a resolution of 0.1 mm was obtained.

EXAMPLE 47

A PTFE film was modified as in Example 15, but was not immersed in hot water nor Soxhlet extracted with THF after the exposure. The contact angle against water was 42°. The film was metallized with the following procedure.

The film was dipped into 0.1 M NaOH for 1 min, rinsed with flowing water, dipped while still wet in a 3% aqueous solution of Cataposit (Registered Trademark of the Shipley Co., Newton, Massachusetts) at 25° C., dipped for 2 min in a 3% aqueous Cataposit solution at 42°-45° C., rinsed for 30 sec in cool flowing tapwater, dipped for 3 min in a 10% aqueous solution of accelerator 19 (Shipley Co.), dipped for 45 sec in Niklad 752 (Registered Trademark, Witco Chemical Corp.), rinsed in cool flowing water, and copper electroplated at 0.016 amp/cm$^2$ for 90 min, when the metal layer was 0.036 mm thick.

The adhesive strength is 4 pounds/inch. If the sample is immersed in hot water for an hour prior to the metal plating the adhesive strength is only 0.15 pounds/inch.

EXAMPLE 48

N,N,-dimethyl aniline does not absorb UV light above 340 nm, while thioxanthon has a absorption maxima at 380 nm. Three DMF solutions were prepared: A contained 0.1 M N,N-dimethylaniline, B contained 0.05 M thioxanthon, and C contained 0.1 M N,N-dimethylanilin+0.05 M thioxanthon. PTFE film was exposed to 366 nm (bandpass filter used) for 1 hour with the same setup as in experiments 1-14. After exposure the films were extensively rinsed with with acetone, and contact angle measured from 25% EtOH in water. Solution A had a contact angle of 73°, B had 77°, and C. had 62°. Pure PTFE has a contact angle of 78°.

EXAMPLE 49

By the same procedure used in Examples 1-14, Teflon ® AF film was exposed to actinic radiation while immersed in a 0.05 M solution of N,N,N',N'-tetramethyl-p-phenylenediamine in N,N-dimethylformamide. After exposure for 1 hr, the contact angle of 25% ethanol in water had decreased 18°.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

I claim:

1. A process for modifying polymer surfaces, comprising, exposing an organic modifier to actinic radiation while a polymer surface is in contact with said organic modifier, provided that the oxidation potential of the modifier minus the reduction potential of the polymer minus the excitation energy of the modifier is less than zero, further provided that said actinic radiation is of a wavelength that is absorbed by said modifier, further provided said polymer does not contain ethylenic unsaturation, and further provided that such modifier does not modify the polymer surface in the absence of actinic radiation:

2. The process as recited in claim 1 wherein said modifier is in a solution in contact with said polymer surface.

3. The process of claim 2 wherein the concentration of said modifier in said solution is about 0.001 to about 0.2M.

4. The process as recited in claim 3 wherein said concentration is about 0.025 to about 0.1M.

5. The process as recited in claim 2 wherein the solvent is a polar aprotic compound.

6. The process as recited in claim 5 wherein said solvent is selected from the group consisting of N,N-dimethylformamide, dimethylsulfoxide, acetonitrile, and dimethylacetamide.

7. The process as recited in claim 1 wherein said modifier is present in the vapor state.

8. The process as recited in claim 1 where said modifier is coated onto said polymer surface.

9. The process as recited in claim 1 wherein said polymer surface is selected from the group consisting of fluorinated polymers, polyimides and polyesters.

10. The process as recited in claim 2 wherein said polymer surface is selected from the group consisting of fluorinated polymers, polyimides and polyesters.

11. The process as recited in claim 9 wherein said polymer surface is a perfluorinated polymer.

12. The process as recited in claim 10 wherein said polymer surface is a perfluorinated polymer.

13. The process as recited in claim 11 wherein said polymer surface is a perfluorinated polymer or copolymer of tetrafluoroethylene.

14. The process as recited in claim 12 wherein said polymer surface is a perfluorinated polymer or copolymer of tetrafluoroethylene.

15. The process as recited in claim 1 wherein said polymer surface and said modifier are selected from the group consisting of: perfluorinated polymers and copolymers of tetrafluoroethylene with the 4-hydroxybenzenethiol dianion, p-aminobenzenethiol anion, benzenethiol anion, the dianion of HSCHRCHROH where R is hydrogen or methyl, the anion of 2,5-pentanedione, the anion of diphenylcarbinol, 2-mercaptoethanol, tetrachlorohydroquinone, 4-aminofluorene, phenylthiazine, cis-stilbene, vanillin, the anion of 2-mercaptoethanol, the anion of 2-naphthol, the anion of dibenzoylmethane, the dianion of ethylene glycol, and N,N,N'N'-tetramethyl-p-phenylenediamine; polyimide based on oxydianiline and pyromellitic anhydride with 4-aminofluorene, the dianion of ethylene glycol, the dianion of 3-hydroxybutane-3-thiol, and vanillin; poly-(ethylene terephthalate) with the anion of 4-aminobenzenethiol; and a copolymer of TFE with perfluoro(2.2- dimethyl-1,3-dioxole) with N,N,N',N'-tetramethyl-p-phenylenediamine.

16. The process as recited in claim 2 wherein said polymer surface and said modifier are selected from the group consisting of: perfluorinated polymers and copolymers of tetrafluoroethylene with the 4-hydroxybenzenethiol dianion, p-aminobenzenethiol anion, benzenethiol anion, the dianion of HSCHRCHROH where R is hydrogen or methyl, the anion of 2,5-pentanedione, the anion of diphenylcarbinol, 2-mercaptoethanol, tetrachlorohydroquinone, 4-aminofluorene, phenylthiazine, cis-stilbene, vanillin, the anion of 2-mercaptoethanol, the anion of 2-naphthol, the anion of dibenzoylmethane, the dianion of ethylene glycol, and N,N,N'N'-tetramethyl-p-phenylenediamine; polyimide based on oxydianiline and pyromellitic anhydride with 4-aminofluorene, the dianion of ethylene glycol, the dianion of 3-hydroxybutane-3-thiol, and vanillin; poly(ethylene terephthalate) with the anion of 4-aminobenzenethiol; and a copolymer of TFE with perfluoro(2,2-dimethyl-1,3-dioxole) with N,N,N',N'-tetramethyl-p-phenylenediamine.

17. The process as recited in claim 1 wherein an accelerator is present, and provided that said actinic radiation is of a wavelength that is absorbed by said accelerator and/or said modifier.

18. The process as recited in claim 2 wherein an accelerator is present, and provided that said actinic radiation is of a wavelength that is absorbed by said accelerator and/or said modifier.

19. The process as recited in claim 17 wherein said accelerator is selected from the group consisting of benzophenone, thioxanthon and naphthalene.

20. The process as recited in claim 18 wherein said accelerator is selected from the group consisting of benzophenone, thioxanthon and naphthalene.

21. The process as recited in claim 1 wherein said modifier oxidation potential minus said reduction potential of the polymer minus said excitation energy of the modifier is more negative than −0.5 volt.

22. The process as recited in claim 2 wherein said modifier oxidation potential minus said reduction potential of the polymer minus said excitation energy of the modifier is more negative than −0.5 volt.

23. The process as recited in claim 1 wherein a pattern of modified and unmodified polymer surface is created.

24. The process as recited in claim 2 wherein a pattern of modified and unmodified polymer surface is created.

25. The process as recited in claim 7 wherein a pattern of modified and unmodified polymer surface is created.

26. The process as recited in claim 1 wherein said polymer surface is modified to varying degrees.

27. The process as recited in claim 2 wherein said polymer surface is modified to varying degrees.

28. The process as recited in claim 7 wherein said polymer surface is modified to varying degrees.

29. The product of the process of claim 1.

30. The product of the process of claim 2.

31. The product of the process of claim 7.

32. The product of the process of claim 1 used to immobilize biologically active molecules.

33. The process as recited in claim 2 wherein said solvent is water or an alcohol.

34. The process as recited in claim 1 comprising the further step of metalizing the modified polymer surface.

35. The product of the process of claim 34.

36. The process of claim 15 wherein said polymer is a copolymer of TFE with perfluoro(2,2-dimethyl-1,3-dioxole) and said modifier is N,N,N',N'-tetramethyl-p-phenylenediamine.

37. The process of claim 16 wherein said polymer surface is a copolymer of TFE with perfluoro(2,2-dimethyl-1,3-dioxole) and said modifier is N,N,N', N'-tetramethyl-p-phenylenediamine.

* * * * *